(12) United States Patent
Brandon et al.

(10) Patent No.: US 9,750,797 B2
(45) Date of Patent: Sep. 5, 2017

(54) SUSTAINED RELEASE VACCINE COMPOSITION

(75) Inventors: Malcolm Brandon, Balwyn (AU); Serge Martinod, Groton, CT (US)

(73) Assignee: VIRBAC CORPORATION, Fort Worth, TX (US)

( * ) Notice: Subject to any disclaimer, the term of this patent is extended or adjusted under 35 U.S.C. 154(b) by 1399 days.

(21) Appl. No.: 11/629,681

(22) PCT Filed: Jun. 16, 2005

(86) PCT No.: PCT/AU2005/000869
§ 371 (c)(1),
(2), (4) Date: Dec. 11, 2007

(87) PCT Pub. No.: WO2005/123120
PCT Pub. Date: Dec. 29, 2005

(65) Prior Publication Data
US 2008/0199491 A1    Aug. 21, 2008

(30) Foreign Application Priority Data

Jun. 16, 2004  (AU) ............................... 2004903283
Feb. 28, 2005  (AU) ............................... 2005900928

(51) Int. Cl.
| | | |
|---|---|---|
| *A61K 39/12* | (2006.01) |
| *A61K 39/02* | (2006.01) |
| *A61K 47/24* | (2006.01) |
| *A61K 39/39* | (2006.01) |
| *A61K 39/08* | (2006.01) |
| *A61K 39/112* | (2006.01) |
| *A61K 9/00* | (2006.01) |
| *A61K 39/108* | (2006.01) |
| *A61K 39/00* | (2006.01) |

(52) U.S. Cl.
CPC ............ *A61K 39/12* (2013.01); *A61K 9/0024* (2013.01); *A61K 9/0092* (2013.01); *A61K 39/02* (2013.01); *A61K 39/0258* (2013.01); *A61K 39/0275* (2013.01); *A61K 39/08* (2013.01); *A61K 39/39* (2013.01); *A61K 47/24* (2013.01); *A61K 2039/521* (2013.01); *A61K 2039/5252* (2013.01); *A61K 2039/5254* (2013.01); *A61K 2039/552* (2013.01); *A61K 2039/55505* (2013.01); *A61K 2039/55577* (2013.01); *C12N 2710/16734* (2013.01); *C12N 2720/12334* (2013.01); *C12N 2750/14334* (2013.01); *C12N 2760/18334* (2013.01); *C12N 2770/20034* (2013.01)

(58) Field of Classification Search
CPC .... A61K 2300/00; A61K 45/06; A61K 38/00; A61K 39/3955; A61K 39/12; A61K 39/0011; A61K 47/42; A61K 9/19; A61K 9/1658; C07K 2317/34; C07K 14/00; C12N 7/00
See application file for complete search history.

(56) References Cited

U.S. PATENT DOCUMENTS

| 5,364,756 | A | * | 11/1994 | Livesey et al. | ................... 435/2 |
| 5,369,019 | A | * | 11/1994 | Foged et al. | ................ 435/69.3 |
| 5,538,733 | A | * | 7/1996 | Emery et al. | ................ 424/422 |

FOREIGN PATENT DOCUMENTS

| WO | WO 99/12568 | * | 3/1999 |
| WO | WO 01/07079 A1 | | 2/2001 |
| WO | WO 03/002102 | * | 1/2003 |
| WO | WO 03/022242 A1 | | 3/2003 |

OTHER PUBLICATIONS

Huang et al., A novel dry powder influenza vaccine and intranasal delivery technology: induction of systemic and mucosal immune responses in rats, 2004, Vaccine, vol. 23, pp. 794-801.*
Dow Corning, Product Information Healthcare Silastic® BioMedical Grade ETR Elastomers (Q7-4720, Q7-4735, Q7-4750, Q7-4765, and Q7-4780) Parts A & B, 2011.*
Challacombe et al., Enhanced secretory IgA and systemic IgG antibody responses after oral immunization with biodegradable microparticles containing antigen, 1992, Immunology, vol. 76, pp. 164-168.*
International Search Report dated Dec. 12, 2006, 4 pages.
Higaki, et al., "Collagen Minipellet as a Controlled Release Delivery System for Tetanus and Diphtheria Toxoid," Vaccine 19 (2001) 3091-3096, Elsevier Science Ltd.
Lofthouse et al., "Injectable Silicone Implants as Vaccine Delivery Vehicles," Vaccine 20:1725-1732 (2002).
Maa et al., "Stabilization of Alum-Adjuvanted Vaccine Dry Powder Formulations: Mechanism and Application" Journal of Pharmaceutical Sciences 92(2):319-332 (2002).
Kemp et al., "Continuous Antigen Delivery From Controlled Release Implants Induces Significant and Anamnestic Immune Responses" Vaccine 20:1089-1098 (2002).
Supplementary European Search Report mailed Aug. 12, 2008 in the International (PCT) Application No. PCT/AU2005000869 which the present application is the U.S. National Stage.

* cited by examiner

*Primary Examiner* — Benjamin P Blumel
(74) *Attorney, Agent, or Firm* — Westerman, Hattori, Daniels & Adrian, LLP (57) ABSTRACT

A non-liquid vaccine composition including one or more antigen component(s); a pharmaceutically acceptable non-liquid adjuvant therefor; and optionally a non-liquid vaccine protection agent.

12 Claims, 2 Drawing Sheets

FIGURE 1

FIGURE 2

SUSTAINED RELEASE VACCINE COMPOSITION

RELATED APPLICATIONS

The present application is a U.S. National Phase Application of International Application PCT/AU2005/000869, filed Jun. 16, 2005, which claims the benefit of Australian Patent Application Nos. 2004903283 filed Jun. 16, 2004 and 2005900928 filed Feb. 28, 2005, all of which are herein incorporated by reference in their entirety for all purposes.

The present invention relates to a vaccine composition, in particular a sustained release vaccine composition, and in particular a sustained release composition in an implant, pellet, tablet, aerosol, powder or granulated form. More specifically, the present invention relates to a sustained release vaccine composition which provides for treatment of various indications at the one time.

Many conventional vaccine compositions require a number of follow-up or booster vaccinations to provide immunity. The necessity for multiple vaccinations for a single disease pathogen may be problematic in that in the case of livestock animals each animal must be handled multiple times to receive the primary and follow-up vaccinations. This multiple handling of the animals is time-consuming and costly. Indeed follow-up vaccinations may be omitted or delayed. Not receiving the follow-up vaccinations may result in the individual not attaining immunity to the disease pathogen.

A number of drug delivery systems are known in the prior art.

For example, a controlled drug-release preparation using as a carrier a hydrophobic polymer material, which is non-degradable after administration into the living body. There are two methods of controlling release of a drug from such preparation; one, using an additive such as an albumin (Japanese patent publication (Tokkohei) No. 61959/1995), and another, by forming an outer layer consisting of hydrophobic polymer alone (Japanese patent publication (Tokkohei) No. 187994/1995).

It would accordingly be a significant advance over the prior art if a vaccine composition could be provided which could provide an improved antibody response rate in vaccinated animals preferably by a single application or administration.

Moreover, in the prior art there is a significant lag time between vaccination and antibody response. If it were possible to generate a more rapid onset of immunity as well as a persistence of immune response over an extended period of time, the nature and scope of potential disease indications that may be treated would be significantly extended.

It is, accordingly, an object of the present invention to overcome or at least alleviate one or more of the difficulties and deficiencies related to the prior art.

In a first aspect of the present invention, there is provided a non-liquid vaccine composition including
   one or more antigen component(s);
   a pharmaceutically acceptable non-liquid adjuvant therefor; and optionally
   a non-liquid vaccine protection agent.

In a preferred aspect of the present invention, there is provided a sustained release vaccine apparatus; the apparatus including:
   a non-liquid vaccine composition including:
     one or more antigen component(s);
     a sustained release support material;
     a pharmaceutically acceptable non-liquid adjuvant therefor; and optionally
     a non-liquid vaccine protection agent
and providing in use, a release rate sufficient to stimulate and/or maintain an immune response.

The term "non-liquid vaccine composition" as used herein refers to a vaccine composition provided in a dry phase form, for example as a solid (including a gel which is not free flowing and is able to hold its shape), a gas, or mixed phase, or is modified to form a dry phase material prior to use or is modified from a dry phase form to a liquid form prior to use.

The vaccine composition may be provided in any suitable form, including an implant, pellet, tablet, capsule, powder, granule, microparticulate or nanoparticulate formulation, aerosol (i.e. a gaseous suspension of fine solid particles), a powder to be dissolved or suspended in a liquid, (e.g. drinking water), or the like. The vaccine composition may be formulated for high speed delivery, for example via a jet injection system. For example the vaccine composition may include components to harden the surface thereof. The vaccine composition may be shaped for high power propulsion delivery.

Applicants have surprisingly found that, by preparing a non-liquid vaccine composition, it is possible to improve the immune response achievable. Whilst we do not wish to be restricted by theory, we postulate that the improved immune response is achieved by the constant release of the antigen component(s) from the non-liquid vaccine composition. The constant release may act to initially prime the immune system, and subsequently boost the immune system. The primary and secondary (booster) stimulation of the immune system may occur following a single application of the non-liquid vaccine composition. Many conventional vaccine compositions require the administration of the primary and booster vaccinations as separate events.

It is further possible to increase the number of antigens that may be included in a single implant, thus providing for a multi-antigen preparation.

More particularly, applicants have found, contrary to the teachings in the prior art, that it is not necessary, when utilising an adjuvant, such as aluminium hydroxide $(Al(OH)_3)$ to provide the adjuvant in an aqueous, gel or other solvent phase.

In a further embodiment of the present invention there is provided a vaccine composition including:
   one or more antigen component(s);
   a pharmaceutically acceptable non-liquid mineral salt adjuvant therefor; and optionally
   a vaccine protection agent.

In a preferred aspect, there is provided a sustained release vaccine apparatus, the apparatus including:
   a vaccine composition including:
     one or more antigen component(s);
     a pharmaceutically acceptable non-liquid mineral salt adjuvant therefor;
     a sustained release support material; and optionally
     a vaccine protection agent
and providing in use, a release rate sufficient to initiate and/or stimulate and/or maintain an immune response.

Applicants have found that the vaccine composition according to this aspect of the present invention may generate, in use, a rapid onset in immunity as well as a maintenance immune response over an extended period of time. Where an immune response has been initiated, e.g. by natural means, the vaccine composition may act as an ongoing stimulant to the immune response. Thus the vaccine composition maintains an immune response over an extended period of time.

The rapid onset of immune response may make possible the treatment of diseases such as animal or human viral, parasitic or bacterial infections including anthrax, rabies, foot and mouth disease, bovine respiratory disease, both prophylactically, and therapeutically once an outbreak has occurred. Similarly treatment of various cancers is particularly preferred.

The sustained release vaccine apparatus may further be utilised in the regulation of physiological processes including growth, reproduction and digestion.

Preferably the sustained release vaccine apparatus may provide approximately zero order release of antigen.

Preferably, the sustained release vaccine apparatus may be formulated to generally mimic the effect of a conventional liquid vaccine, without the need for a cold chain, or bulky liquid components. The vaccine apparatus accordingly may provide significant advantages in formulation and handling.

The sustained release vaccine apparatus may be in the form of a mini-implant or pellet. Preferably the sustained release mini-implant(s) or pellet(s) in combination may provide a blood level of antigen at least equal to a predetermined threshold for an extended period, e.g. of approximately 1 to 52 weeks, preferably 1 to 26 weeks, for a selected indication.

Each sustained release vaccine apparatus according to the present invention is biocompatible and may optionally be biodegradable.

The vaccine composition, as described above, includes one or more antigen component(s). The antigen component(s) according to the present invention may, for example, include components selected from polypeptides, proteins, protein fragments, DNA or RNA fragments, hapten-carrier combinations, oligosaccharides or polysaccharides, oligonucleotides or polynucleotides, live attenuated viruses and/or bacteria, other antigenic compounds or a DNA/RNA sequence coding for any of the above. For example, these may be derived from pathogenic organisms such as viruses, bacteria, parasites or the like, and may optionally comprise a fragment of an antigen originating from these organisms, or they may be prepared synthetically and correspond to natural antigenic determinants, or may be derived from these.

The antigen component(s) may preferably include a component active against one or more disease pathogens, for example, any pathogenic, bacterial, viral (DNA or RNA), protozoan, mycoplasma or parasitic disease. For example, the disease pathogen may be selected from the group consisting of, but not limited to:

| | |
|---|---|
| Adenovirus | AIDS |
| Anthrax | BCG |
| Chlamydia | Cholera |
| Circovirus | Classical swine fever |
| Coronavirus | Diphtheria-Tetanus (DT for children) |
| Diphtheria-Tetanus (tD for adults) | Distemper virus |
| DTaP | DTP |
| E coli | Eimeria (coccidosis) |
| Encephalitis | Feline immunodeficiency virus |
| Feline leukemia virus | Foot and mouth disease |
| Hemophilus | Hepatitis A, B, C, D, E, F |
| Hepatitis B/Hib | Herpes virus |
| Hib | Influenza |
| Japanese Encephalitis | Lyme disease |
| Measles | Measles-Rubella |
| Meningococcal | MMR |
| Mumps | Mycoplasma |
| Para influenza virus | Parvovirus |
| Pasteurella | Pertussis |
| Pestivirus | Plague |
| Pneumococcal | Polio (IPV) |
| Polio (OPV) | Pseudorabies |
| Rabies | Respiratory syncitial virus |
| Rhinotracheiitis | Rotavirus |
| Rubella | *Salmonella* |
| SARS | Tetanus |
| Typhoid | Varicella |
| Viral diarrhoea virus | Yellow Fever |

The antigen component(s) may include an inactivated parvovirus, inactivated rhinotraceiitis, inactivated viral diarrhoea virus, a tetanus toxoid antigen, clostridial antigens or combinations thereof.

The vaccine composition may include from 1 to 12, or more antigen component(s), preferably 2 to 8 antigen components, more preferably 3 to 7 antigen components.

The antigen component(s) may be present in the vaccine composition in any suitable amounts. The antigen component(s) may be present in amounts of approximately 0.1 to 50% by weight, preferably approximately 0.1 to 40% by weight, more preferably approximately 0.1 to 5% by weight, based on the total weight of the vaccine composition.

As stated above, the vaccine composition further includes a pharmaceutically acceptable, preferably non-liquid, adjuvant. The adjuvant may be of any suitable type. Use of the preferred non-liquid adjuvant allows elimination of a cold chain and/or bulky liquid components, as well as avoiding the necessity for processes of adjuventing the vaccine formulation.

By the term "adjuvant" we mean any substance that enhances the immune response to an antigen. Adjuvants useful in the vaccine composition according to the present invention include mineral compounds including mineral salts such as calcium or aluminium salts, mineral or non-mineral oils, bacterial products, liposomes, saponins, iscoms and biodegradable microparticles.

By the term "non-liquid adjuvant" as used herein, we mean an adjuvant which is provided as a solid form, or is modified to form a solid, prior to incorporation in the vaccine composition, or is modified from a solid form to a liquid or solution form prior to incorporation in the vaccine composition.

Such adjuvants are well known in the art and include mineral salts, saponins such as Quil A, mineral oils such as Marcol 52 non-mineral oils, such as Montanide 103 (SEPPIC, Paris, and pluronic polymers, such as L121 (BASF, N.J.).

In certain embodiments, the vaccine composition may include other adjuvants, including adjuvants in liquid form. Such other adjuvants that may be used include squalene and squalene, Adjuvant 65 (containing peanut oil, mannide monooleate and aluminium monostearate), surfactants such as hexadecylamine, octadecylamine, lysolecithin, dimethyldioctadecylammonium bromide, N,N-dioctradecyl-N,N$^1$-bis(2-hydroxyethyl)-propanediamine, methoxy-hexadecyl-glycerol and pluronic polyols, polyanions such as pyran, dextran sulfate, polyacrylic acid and carbopol, peptides and amino acids such as muramyl dipeptide, demethylglycine, tuftsin and trehalose dimycolate, Adju-Phos, Algal Glucan, Algammulin, aluminium salts including aluminium hydroxide ($Al(OH)_3$), aluminium phosphate ($AlPO_4$), Alhydrogel, Antigen Formulation, Avridine, Bay R1005, Calcitriol, Calcium Phosphate, Calcium Phosphate Gel, Cholera Holotoxin (CT), Cholera Toxin B Subunit (CTB), CRL1005, DDA, DHEA, DMPC, DMPG, DOC/Alum Complex, Gamma Inulin, Gerbu Adjuvant, GMDP, Imiquimod, ImmTher, Interferon-gamma, Iscoprep 7.0.3, Loxoribine, LT-OA or LT Oral Adjuvant, MF59, Mannan, MONTANIDE ISA 51, MONTANIDE ISA 720, MPL, MTP-PE, MTP-PE, Murametide, Murapalmitine, D-Murapalmitine, NAGO, Nonionic Surfactant Vesicles, Pleuran, PLGA, PGA and PLA, Pluronic L121, PMMA, PODDS, Poly Ra: Poly rU, Polyphosphazene, Polysorbate 80, Protein Cochleates, QS-21, Quil A, Rehydragel HPA, Rehydragel LV, S-28463, SAF-1, Sclavo Peptide, Sendai Proteoliposomes, Sendai-Containing Lipid Matrices, Span 85, Specol, Stearyl Tyrosine, Theramide, Threonyl-MDP and Ty Particles.

The pharmaceutically acceptable adjuvant preferably includes a mineral salt, for example a dry calcium or aluminium salt, e.g. $Ca_3(PO_4)_2$, $Al(OH)_3$ or $AlPO_4$ and/or a saponin.

In other embodiments, where the vaccine composition is other than a non-liquid vaccine composition, the non-liquid adjuvant is selected from one or more mineral salts. Preferably, the mineral salt is selected from one or more calcium or aluminium salts. More preferably the adjuvant is selected from one or more of calcium phosphate, aluminium phosphate and aluminium hydroxide.

The adjuvant may be present in amounts of approximately 0.1% to 30% by weight, preferably approximately 0.1% to 30% by weight, more preferably approximately 0.1% to 5% by weight, based on the total weight of the vaccine composition.

As stated above, the vaccine composition may preferably include a vaccine protection agent.

The vaccine protection agent may function to 'chaperone' the antigen and allow regulation of the release rate of the antigen and/or adjuvant. The vaccine protection agent is in a non-liquid form and may include a protein, preferably an animal protein including whole serum or fractions thereof.

The vaccine protection agent, in a preferred aspect, may be selected to function, in addition, to provide or enhance a passive immunity to a disease indication.

An immunoglobulin (including monoclonal antibodies), for example γ-globulin, more preferably a human or animal γ-globulin may be used. The immunoglobulin may be selected to provide specific antibody activity against a specific disease.

The vaccine protection agent may be present in relatively large amounts. The vaccine protection agent may be present in amounts of approximately 10 to 60% by weight, preferably approximately 10 to 40% by weight, based on the total weight of the vaccine composition.

Accordingly, in a preferred aspect of the present invention, the non-liquid vaccine composition may include
a plurality of antigen components;
a pharmaceutically acceptable non-liquid adjuvant; and optionally
a non-liquid vaccine protection agent.

The antigen components may be selected from an inactivated parvovirus, rhinotraceiitis, viral diarrhoea virus, tetanus toxoid antigen, clostridial antigens or a combination thereof. A combination of 2 to 12, more preferably 3 to 7 antigen components may be used.

The pharmaceutically acceptable adjuvant may include a calcium or an aluminium salt, e.g. aluminium hydroxide or aluminium phosphate, in a non-liquid form.

In a further preferred embodiment of the present invention there is provided a vaccine composition including
a plurality of antigen components;
a pharmaceutically acceptable non-liquid mineral salt adjuvant therefor; and optionally
a vaccine protection agent.

The vaccine protection agent may include an immunoglobulin (including monoclonal antibodies), preferably a γ-globulin, that may function to provide, or enhance, passive immunity against a specified disease.

When the vaccine composition is other than a non-liquid vaccine composition, the non-liquid mineral salt adjuvant may be selected from one or more calcium or aluminium salts, more preferably one or more of calcium phosphate, aluminium phosphate and aluminium hydroxide.

The vaccine composition may further include a pharmaceutically acceptable carrier.

The pharmaceutical carrier may be selected to assist release of the antigen component(s) over an extended period of time from the composition.

The carrier may include a water-soluble or water-insoluble substance.

A water-soluble substance is a substance which plays a role in controlling infiltration of water into the interstices of the drug dispersion. There is no restriction in terms of the water-soluble substance other than that it is in a non-liquid state, once formulated, at the body temperature of the animal or human being to which it is to be administered, and is physiologically acceptable and water-soluble.

One water-soluble substance, or a combination of two or more water-soluble substances may be used. The water-soluble substance specifically may be selected from one or more of the group consisting of synthetic polymers (eg. polyethylene glycol, polyethylene polypropylene glycol), sugars (eg. sucrose, mannitol, glucose, sodium chondroitin sulfate), polysaccharides (e.g. dextran), amino acids (eg. glycine and alanine), mineral salts (eg. sodium chloride), organic salts (eg. sodium citrate) and proteins (eg. gelatin and collagen and mixtures thereof).

In addition, when the water-soluble substance is an amphipathic substance, which dissolves in both an organic solvent and water, it has an effect of controlling the release of, for example, a lipophilic drug by altering the solubility thereof. An amphipathic substance includes, but not limited to, one or more selected from the group consisting of polyethylene glycol or a derivative thereof, polyoxyethylene polyoxypropylene glycol or a derivative thereof, fatty acid ester and sodium alkylsulfate of sugars, and more specifically, polyethylene glycol, polyoxy stearate 40, polyoxyethylene-[196]polyoxypropylene [67]glycol, polyoxyethylene [105] polyoxypropylene[5]glycol, polyoxyethylene[160] polyoxypropylene[30]glycol, sucrose esters of fatty acids, sodium lauryl sulfate, sodium oleate, sodium chloride, sodium desoxycholic acid (or sodium deoxycholic acid (DCA)) of which mean molecular weights are more than 1500.

Polyoxyethylene polyoxypropyleneglycol, sucrose, sodium chloride or DCA or a mixture of two or more thereof are preferred.

In addition, the water-soluble substance may include a substance selected from one or more of the group consisting of drugs, peptides, proteins, glycoproteins, polysaccharides, or an antigenic substance used as vaccines.

A water-insoluble carrier, when present, may include a substance which plays a role in controlling infiltration of water into the interstices of the drug dispersion. There is no restriction in terms of the water-insoluble substance, other than that it is in a non-liquid state, once formulated, at the body temperature of the animal or human being to which it is to be administered, and is physiologically acceptable. One water-insoluble substance, or a combination of two or more water-insoluble substances may be used.

The water-insoluble substance specifically may be selected from one or more of the group of water insoluble polymers, resins and latexes including water-insoluble acrylates, methacrylates and other carboxy polymers, waxes, lipids including phospholipids and lipoproteins.

The pharmaceutical carrier may constitute from approximately 1% to 20% by weight, preferably approximately 10% to 20% by weight, based on the total weight of the vaccine composition.

The vaccine composition may further include a pharmaceutically active component. The pharmaceutically active component may include a water-insoluble pharmaceutical, a water-soluble pharmaceutical or mixtures thereof.

The water-soluble antigens useful in the sustained release delivery apparatus according to the present invention include such drugs as peptides, polypeptides, proteins, glycoproteins, polysaccharides, and nucleic acids.

The present invention is particularly appropriate for pharmaceuticals that are very active even in extremely small quantities and whose sustained long-term administration is sought. When used in substantially increased quantities, such pharmaceuticals may be applied to disease indications heretofore untreatable over an extended period. The pharmaceuticals may be exemplified by, but not limited to, one or more selected from the group consisting of cytokines (eg. interferons and interleukins), hematopoietic factors (eg. colony-stimulating factors and erythropoietin), hormones (eg. growth hormone, growth hormone releasing factor, calcitonin, leuteinizing hormone, leuteinizing hormone releasing hormone (LHRH), and insulin), growth factors (eg. somatomedin, nerve growth factor), neurotrophic factors, fibroblast growth factor, and hepatocyte proliferation factor; cell adhesion factors; immunosuppressants; enzymes (eg. asparaginase, superoxide dismutase, tissue plasminogen activating factor, urokinase, and prourokinase), blood coagulating factors (eg. blood coagulating factor VIII), proteins involved in bone metabolism (eg. BMP (bone morphogenetic protein)), and antibodies. A growth hormone or growth factor is particularly preferred.

The interferons may include alpha, beta, gamma, or any other interferons or any combination thereof. Likewise, the interleukin may be IL-1, IL-2, IL-3, or any others, and the colony-stimulating factor may be multi-CSF (multipotential CSF), GM-CSF (granulocyte-macrophage CSF), G-CSF (granulocyte CSF), M-CSF (macrophage CSF), or any others.

Pharmaceuticals that may be included in the vaccine compositions according to the present invention may be further exemplified by low-molecular-weight drugs such as water-soluble anticancer agents, antibiotics, anti-inflammatory drugs, alkylating agents, and immunosuppressants. Examples of these drugs include adriamycin, bleomycins, mitomycins, fluorouracil, peplomycin sulfate, daunorubicin hydrochloride, hydroxyurea, neocarzinostatin, sizofuran, estramustine phosphate sodium, carboplatin, beta-lactams, tetracyclines, aminoglycosides, and phosphomycin.

The vaccine composition of the present invention may contain two or more drugs depending on the disease and method of application.

Water-insoluble pharmaceutically active components which may be utilised in the sustained release delivery apparatus according to the present invention include lypophilic pharmaceuticals.

Depending on the disease(s) or method for application, multiple lipophilic drugs may be included.

The pharmaceutically active component may be present in the vaccine composition in relatively small amounts. The pharmaceutically active component may be present in amounts of from approximately 1 to 25% by weight, preferably approximately 1 to 5% by weight, based on the total weight of the vaccine composition.

Each sustained release vaccine apparatus may include additional carriers or excipients, lubricants, fillers, plasticisers, binding agents, colourants and stabilising agents.

Suitable fillers may be selected from the group consisting of talc, titanium dioxide, starch, kaolin, cellulose (microcrystalline or powdered) and mixtures thereof.

The sustained release vaccine apparatus may be of any shape and may be administered by any method for vaccine delivery known in the art. For example, the apparatus may be formulated for delivery by a method selected from the group consisting of, but not limited to, implantation, injection, aerosol, high power propulsion, including jet injection, and the like.

Preferably, the apparatus may be formulated for vaccine delivery to a suitable site, e.g. via an intramuscular, subcutaneous, intradermal, intraperitoneal, transdermal, intravenous or similar route.

The sustained release vaccine apparatus may be in the form of a mini-implant or pellet. The mini-implant or pellet may preferably be of the covered rod or matrix type. An extruded rod is preferred. A covered, extruded rod-like shape is preferred.

The size, number, length, diameter and payload of the mini-implant(s) or pellet(s) may vary with the pharmaceutically active component and/or antigen selected.

The optimum combination of size, number and payload may be established through simple experiment.

For example, in veterinary applications, a typical sheep implant according to the present invention may have dimensions of approximately 1.5 mm outer diameter×2 cm in length.

Preferably the sustained release delivery apparatus may provide approximately zero order release of antigen.

Preferably, the sustained release delivery apparatus may be formulated to mimic the effect of a conventional liquid vaccine, without the need of a cold chain or bulky liquid formulation.

The sustained release support material may take the form of a support matrix or rod, preferably a covered rod structure. The sustained release support material may take the form of an open ended cylindrical rod.

The sustained release support material may be formed from a biodegradable or biocompatible material, preferably a biocompatible hydrophobic material. The biocompatible material may be selected from the group consisting of polyesters, polyamino acids, silicones, ethylene-vinyl acetate copolymers and polyvinyl alcohols. Preferably the sustained release support material is a silicone material. A silicone rod is preferred. The silicone material may be a porous silicon or Biosilicon material, for example as described in International patent application PCT/GB99/01185, the entire disclosure of which is incorporated herein by reference. A mesoporous, microporous or polycrystalline silicone or mixtures thereof may be used.

Biodegradable polymers that may be employed in the present invention may be exemplified by, but not limited to, polyesters such as poly(lactic acid-glycolic acid) copolymers (PLGA), hydrophobic polyamino acids such as polyaranin, polyleucine, polyanhydride, poly(glycerol-sebacate) (PGS), Biopol, Pluronic polyols (Poloxamers) and the like. The hydrophobic polyamino acids mean polymers prepared from hydrophobic amino acids.

Nonbiodegradable polymers that may be employed in the present invention may be exemplified by, but not limited to, silicones, polytetrafluoroethylenes, polyethylenes, polypropylenes, polyurethanes, polyacrylates, polymethacrylates such as polymethylmethacrylates, etc., ethylene-vinyl acetate copolymers, and others.

More preferably a silicone elastomer as described in International patent application PCT/AU02/00865, to applicants (the entire disclosure of which is incorporated herein by reference), may be used. For example the silicone elastomer may be formed from a methyl-vinyl siloxane polymer including a fumed silica as reinforcing filler. The sustained release support material may comprise approximately 30 to 85% by weight, preferably approximately 35 to 50% by weight, of the sustained release apparatus, the remainder formed of the vaccine composition.

Suitable binding agents include polyvinyl pyrrolidine, hydroxypropyl cellulose and hydroxypropyl methyl cellulose and mixtures thereof.

The sustained release implant according to the present invention may have a rod-like shape, for example it is selected from circular cylinders, prisms, and elliptical cylinders. When the device is administered using an injector-type instrument, a circular cylindrical device is preferred since the injector body and the injection needle typically have a circular cylindrical shape.

The sustained release implant according to the present invention may be manufactured according to International patent application PCT/AU2002/000868 entitled "Preparation of sustained release pharmaceutical composition", to Applicants, the entire disclosure of which is incorporated herein by reference.

The inner layer of the pharmaceutical formulation of the present invention, viewed in right section, may contain two or more layers containing different water-soluble pharmaceuticals. These layers may take the form of concentric circles with a single center of gravity or may appear as a plural number of inner layers whose respective centers of gravity lie at different points in the cross section. When the pharmaceutical formulation contains more than one inner layer there may be one or more pharmaceuticals present in the inner layers. For example, the pharmaceuticals may be present such that each layer contains a different pharmaceutical or there is more than one pharmaceutical in one or all of the inner layers.

For example using an injector-type instrument, the configuration may be circular cylindrical, and the cross-sectional diameter in the case is preferably 0.2 to 5 mm, preferably approximately 0.5 to 5 mm, more preferably approximately 1 to 2 mm. The axial length is preferably approximately 0.2 to 40 mm, preferably 0.5 to 30 mm, more preferably 1 to 20 mm.

Sustained release implants according to the present invention may preferably have a double-layer structure, in order to achieve long-term zero-order release.

The double layer structure may include
an antigen-containing inner layer; and
a water impermeable outer layer.

The water impermeable outer layer may be formed of a silicone material. More preferably water-impermeable outer layers may be formed from a liquid coating composition including a liquid siloxane component.

Applicants have surprisingly found that the sustained release implants having a double layer structure exhibit an unexpected release profile. Contrary to expectations, the maximum serum levels vary with the length of implant, not merely the time period over which sustained release is maintained. Whilst we do not wish to be restricted by theory, it is postulated that, particularly for small molecules, release is occurring not only from the open ends of the covered rod implant but also through the water-impermeable outer layer.

Such a release mechanism provides significant freedom in designing both the rate and time of release by simply varying implant length. Thus, for example, implants of varying sizes may be included to deliver a variety of desired treatment regimes.

Where a double-layer structure is used, the pharmaceutical-containing inner layer and the water-impermeable outer layer may be fabricated separately or simultaneously.

Desirably the rod-like implant includes an outer coating layer. The thickness of the outer layer should be selected as a function of the material properties and the desired release rate. The outer layer thickness is not critical as long as the specified functions of the outer layer are fulfilled. The outer layer thickness is preferably approximately 0.05 mm to 3 mm, more preferably 0.05 mm to 0.25 mm, and most preferably 0.05 mm to 0.1 mm.

A pharmaceutical formulation with an open end at one terminal only may be fabricated by dipping one terminal of the pharmaceutical formulation into a solution which dissolves the outer-layer material and drying it, or by covering one terminal end of the pharmaceutical formulation with a cap made from the outer-layer material. In addition, the fabrication may comprise insertion of the inner layer into an outer-layer casing with a closed-end at one terminal, which are separately produced, and also formation of the inner layer in said casing.

In a further preferred aspect of the present invention, there is provided a sustained release kit including
a vaccine delivery apparatus; and
a sustained release liquid or non-liquid vaccine composition as described above.

The vaccine delivery apparatus may be of any suitable type. Any suitable delivery apparatus may be used. An injection instrument is preferred. A high speed injection instrument is preferred. For example, in veterinary applications, an injector instrument for subcutaneous delivery may be used as the sustained release delivery apparatus.

For example, multiple pellets or tablets may be provided in a single cartridge for use in a standard injector instrument which in turn lodge as individual mini-pellets within the body of the animal to be treated.

In a further preferred form of the present invention, the plurality of sustained release implants may be provided in a biodegradable sheath. The biodegradable sheath may be formed of a water-soluble material.

The water-soluble material utilised in the biodegradable sheath may be selected from one or more of the water-soluble substances described below.

In a further aspect of the present invention there is provided a method for the therapeutic or prophylactic treatment of an indication in an animal (including a human) requiring such treatment, which method includes administering to the animal a non-liquid vaccine composition including
one or more antigen component(s);
a pharmaceutically acceptable non-liquid adjuvant therefor; and optionally
a non-liquid vaccine protection agent and/or
a pharmaceutically acceptable carrier.

In a preferred aspect, the method may include administering to the animal a sustained release vaccine apparatus including:
a non-liquid vaccine composition including:
one or more antigen component(s);
a pharmaceutically acceptable non-liquid adjuvant therefor;
a sustained release support material; and optionally
a non-liquid vaccine protection agent and/or
a pharmaceutically acceptable carrier
such that an immune response is initiated and/or stimulated and/or maintained.

The sustained release vaccine composition may be provided in any suitable form, including an implant, pellet, tablet, capsule, powder, granule, aerosol or the like. The vaccine composition may be formulated for high speed delivery, for example via a jet injection system. For example the vaccine apparatus may include components to harden the surface thereof. The vaccine apparatus may be shaped for high power propulsion delivery.

As stated above, it has been found that the vaccine composition may provide, in use, an enhanced immune response. The vaccine composition may further provide a rapid onset of immunity and a persistence in immune response over an extended period of time. Protection may be achieved against a plurality of disease indications in a one-shot treatment and without the necessity for follow-up or booster vaccinations.

Accordingly, in a preferred embodiment of this aspect of the present invention, the non-liquid vaccine composition may include

- a plurality of antigen components;
- a pharmaceutically acceptable non-liquid adjuvant therefor; and
- a non-liquid vaccine protection agent.

In a further embodiment of the present invention there is provided a method for the therapeutic or prophylactic treatment of an indication in an animal (including a human) requiring such treatment, which method includes administering to the animal a vaccine composition including

- one or more antigen component(s);
- a pharmaceutically acceptable non-liquid mineral salt adjuvant therefor; and optionally
- a vaccine protection agent and/or
- a pharmaceutically acceptable carrier.

In a preferred aspect, the method may include administering to the animal a sustained release vaccine apparatus including:

- a vaccine composition including:
  - one or more antigen component(s);
  - a pharmaceutically acceptable non-liquid mineral salt adjuvant therefor;
  - a sustained release support material; and optionally
  - a non-liquid vaccine protection agent and/or
  - a pharmaceutically acceptable carrier such that an immune response is initiated and/or stimulated and/or maintained.

In a preferred embodiment of this aspect of the present invention, the liquid vaccine composition may include

- a plurality of antigen components;
- a pharmaceutically acceptable non-liquid mineral salt adjuvant therefor; and optionally
- a vaccine protection agent and/or
- a pharmaceutically acceptable carrier.

The antigen components may be selected from any antigen of a pathogen, for example, an inactivated parvovirus, rhinotraceiitis, viral diarrhoea virus, tetanus toxoid antigen, clostridial antigens or a combination thereof.

The pharmaceutically acceptable adjuvant may include a dry calcium or aluminium salt, such as aluminium hydroxide, and the pharmaceutical protection agent may include an immunoglobulin (including monoclonal antibodies), preferably a γ-globulin, that may function to provide, or enhance, passive immunity against a specified disease.

In a preferred embodiment, the vaccine composition may be utilised in prophylactic and/or therapeutic treatment of multiple diseases such as anthrax, rabies, foot and mouth disease, or bovine respiratory disease, both prophylactically and therapeutically, once an outbreak has occurred.

The method of administration may be of any means, for example, including implantation, injection (for example, subcutaneous or intramuscular injection, intradermal injection, intraperitoneal injection), aerosol, high power propulsion, intraocular insertion, insertion into the ear, intranasal insertion or indwelling, intravaginal or intradwelling, intrarectal insertion or indwelling, for example as a suppository or utilising oral administration.

The animals to be treated may be selected from the group consisting of sheep, cattle, goats, horses, camels, pigs, dogs, cats, ferrets, rabbits, marsupials, buffalos, yaks, primates, humans, birds including chickens, geese, ducks and turkeys, rodents including rats and mice, fish, reptiles and the like.

The present invention will now be more fully described with reference to the accompanying examples and figure. It should be understood, however, that the description following is illustrative only and should not be taken in anyway as a restriction on the generality of the invention described above.

In the Figures:

FIG. 1 is a graph showing titres for ovalbumin (OVA) antibodies as described in Example 3.

FIG. 2 is a graph showing titres for *Salmonella* antibodies as described in Example 4.

EXAMPLE 1

A mixture of Tetanus Toxoid Antigen, Saponin, Human Gamma Globulin and NaCl in proportions specified in Table 1 below was produced. The obtained solid was milled and passed through a sieve. A portion of a powder thus obtained and Silastic™ Medical Grade ETR Elastomer Q7-4750 Component A and Silastic™ Medical Grade ETR Elastomer Q7-4750 component B were mixed to give a drug dispersion component. Silastic™ Medical Grade ETR Elastomer Q7-4750 Component A and Silastic™ Medical Grade ETR Elastomer Q7-4750 Component B were mixed to give a coating layer component. Thus obtained drug dispersion component and coating layer component were molded by extruding from a double extruder which enables them to be molded by extruding so that the drug dispersion is concentrically coated with the coating layer, and was allowed to stand at room temperature to cure, which was cut to obtain the cylindrical preparation 1 (the length of the preparation is 1.0 or 2 cm, the external diameter of the preparation is 1.5 mm) (See Table 2). Silicone comprised the other 50% of the formulation.

TABLE 1

| Type | Outer Diameter (mm) | Powder (%) | Composition/Powder (%) TET | SAP | γ-Glob | NaCl |
|---|---|---|---|---|---|---|
| CR | 1.5 | 50 | 2.68 | 2.68 | 34.64 | 10 |

Abbreviations
CR = covered rod
TET = Tetanus Toxoid Antigen 100 doses @ 384 ug/dose = 38.4 mg total weight Each dose contains 6Lf (flock units) of tetanus toxoid, which was freeze dried with 200 ug/dose of trehalose to provide some stability and bulk for handling.
γ-Glob = Human Gamma Globulin
SAP = Saponin adjuvant
Outer diameter, mm = 1.5 mm
Inner diameter, mm = 1.3 mm The cylindrical preparation 1 is then cut into various lengths as shown in Table 2 to provide the sustained release mini-pellets according to the present invention.

TABLE 2

Design:

| Total Length | Implant Length | |
|---|---|---|
| | 1.0 cm | 2.0 cm |
| | Number of implants | |
| 2 cm | 2 | — |
| 2 cm | — | 1 |
| 4 cm | 4 | — |
| 4 cm | — | 2 |

1 ml s.c day 0 and day 28

Groups
Group 1—1 cm×2 n=6
Group 2—2 cm×1 n=3
Group 3—1 cm×4 n=6
Group 4—2 cm×2 n=2
Group 5—Controls—Glanvac 6 in 1.

Examination 1

Preparation 1 was subcutaneously administered to Merino and Merino cross sheep, whole blood was collected from the animal via the jugular vein, and then, the concentration of antibody in the plasma was determined by antibody titration.

Animals: Merino/Merino Cross Sheep
Identification: Ear tags—both ears
Implants: Single formulation
Tetanus toxoid—containing 384 microgram of antigen per cm of implant
Cured at 37° C. for 3 days
Adjuvant—Saponin
Type: Covered rod
Dose: Two doses to be investigated—2 cm and 4 cm
Size: Implants used will be cut to 1.0 or 2.0 lengths
Site: Neck—at the base of the ear.

Blood samples to be collected at 0, 7, 14, 21, 28, 42, 56, 84, 91 and 210 days

Sheep were allocated to 5 treatment groups as outlined in Table 3.

TABLE 3

| Group Number | Sample Numbers |
|---|---|
| 1 | 2, 4, 5, 16, 17, 19 |
| 2 | 6, 7, 21 |
| 3 | 1, 11, 13, 18, 20, 22 |
| 4 | 10, 23 |
| 5 | 3, 8, *9, 12, 14, 15, |

*Sheep euthanased 19/9/03 28 days - no more samples after this

The results are provided in Table 4.

TABLE 4

Merino/Merino Cross Sheep Sera, Trial - O-03-001
Technical Standard
All titres are IU/ml

| | Day 14 | Day 42 | Day 56 | Day 91 | Day 210 |
|---|---|---|---|---|---|
| Sample ID - Group 1 | | | | | |
| 2 | 7.72 | 4.48 | 5.68 | N/S | 4.26 |
| 4 | 28.24 | 1.22 | 0.79 | 5.4 | 7.44 |
| 5 | 6.22 | 24.2 | 17.06 | 1.49 | N/S |
| 16 | 4.23 | 7.77 | 5.26 | 4.48 | 4.47 |
| 17 | N/S | 8.46 | 8.47 | 16.75 | 5.54 |
| 19 | 5.8 | 8.56 | 3.65 | 3.82 | 3.38 |
| GMT | 8.02 | 6.49 | 4.81 | 4.71 | 4.84 |
| Sample ID - Group 2 | | | | | |
| 6 | 12.95 | 0.2 | 0.19 | 9.29 | 1.42 |
| 7 | 20.37 | 7.39 | 3.58 | 3.55 | 1.33 |
| 21 | 9.19 | 5.12 | 2.96 | N/S | 6.29 |
| GMT | 13.43 | 1.96 | 1.26 | 5.74 | 2.28 |
| Sample ID - Group 3 | | | | | |
| 1 | 7.8 | 6.97 | 5.53 | 4.41 | 5.32 |
| 11 | 18.72 | 12.86 | 6.86 | 3.48 | 3.47 |
| 13 | 1.01 | 2.24 | 3.29 | 1.43 | 5.36 |
| 18 | 9.14 | 7.6 | 3.34 | 5.05 | 1.63 |
| 20 | 9.7 | 12.38 | 6.69 | 6.3 | 7.3 |
| 22 | 28 | 15.8 | 8.55 | 5.88 | 9.08 |
| GMT | 8.46 | 9.64 | 5.36 | 4.00 | 4.69 |
| Sample ID - Group 4 | | | | | |
| 10 | 10.44 | 19.4 | 14.18 | N/S | 2.79 |
| 23 | 21.8 | 9.65 | 13.52 | 7.49 | 5.88 |
| GMT | 15.09 | 13.68 | 13.85 | 7.49 | 4.05 |
| Sample ID - Group 5 | | | | | |
| 3 | 1.82 | 25.55 | 0.71 | 2.86 | 4.11 |
| 8 | 0.14 | N/S | N/S | N/S | N/S |
| 9 | 0.36 | 10.55 | 4.43 | 8.3 | 2.13 |
| 12 | 23.28 | 13.1 | 6.84 | 1.01 | 4.99 |
| 14 | 7.48 | 6.33 | 3.62 | 1.66 | 6.93 |
| 15 | 24.61 | 27.6 | 11.8 | 4.01 | 3.51 |
| GMT | 2.71 | 14.39 | 3.91 | 2.76 | 4.03 |

N/S = no sample

Groups
Group 1—cm×2 n=6
Group 2—2 cm×1 n=3
Group 3—1 cm×4 n=6
Group 4—2 cm×2 n=2
Group 5—Controls—Glanvac 6 in 1.

Conclusions

1 The use of implants, the subject of the present invention (the division of a single larger implant into multiple small implants) results in a higher serum level of antibody in a more rapid time frame (see Table 4).

2 Optimum results were achieved with the Group 4, 2 cm×2 implant combination. The results with the Group 3 and Group 1 combination showed some sustained immune response, but the Group 2 combination failed to provide sustained immunity.

EXAMPLE 2

Example 1 was repeated utilising the vaccine composition formulations specified in Table 5 below.

Mixtures of antigen and adjuvant (Saponin) or aluminium hydroxide in proportions specified in Table 5 below was produced.

TABLE 5

| 1: Canine parvovirus 2a inactivated virus: | |
|---|---|
| antigen (freeze-dried) | 30% |
| adjuvant (saponin) | 10% |
| silicone formulation | 60% |

TABLE 5-continued

| 2: canine parvovirus 2a inactivated virus: | |
|---|---|
| antigen (freeze-dried) | 30% |
| adjuvant (powdered Al(OH)$_3$) | 10% |
| silicone formulation | 60% |
| 3: bovine rhinotracheiitis vaccine modified - live: | |
| antigen | 15% |
| adjuvant (saponin) | 1% |
| silicone formulation | 84% |
| 4: bovine rhinotracheiitis vaccine modified 0 live: | |
| antigen | 15% |
| adjuvant (powdered Al(OH)$_3$) | 1% |
| silicone formulation | 84% |

The obtained solid was milled and passed through a sieve. A portion of a powder thus obtained and Silastic™ Medical Grade ETR Elastomer Q7-4750 Component A and Silastic™ Medical Grade ETR Elastomer Q7-4750 component B were mixed to give a drug dispersion component. Silastic™ Medical Grade ETR Elastomer Q7-4750 Component A and Silastic™ Medical Grade ETR Elastomer Q7-4750 Component B were mixed to give a coating layer component. Thus obtained drug dispersion component and coating layer component were molded by extruding from a double extruder which enables them to be molded by extruding so that the drug dispersion is concentrically coated with the coating layer, and was allowed to stand at room temperature to cure, which was cut to obtain the cylindrical preparation (the length of the preparation is 1.0 or 2 cm, the diameter of the preparation is 1.5 mm).

EXAMPLE 3

A mixture of Ovalbumin, Gamma Globulin, NaCl and Aluminium hydroxide or Saponin in proportions specified in Table 6 below was produced. The obtained solid was milled and passed through a sieve. A portion of a powder thus obtained and Silastic™ Medical Grade ETR Elastomer Q7-4750 Component A and Silastic™ Medical Grade ETR Elastomer Q7-4750 component B were mixed to give a drug dispersion component. Silastic™ Medical Grade ETR Elastomer Q7-4750 Component A and Silastic™ Medical Grade ETR Elastomer Q7-4750 Component B were mixed to give a coating layer component. Thus obtained drug dispersion component and coating layer component were molded by extruding from a double extruder which enables them to be molded by extruding so that the drug dispersion is concentrically coated with the coating layer, and was allowed to stand at room temperature to cure, which was cut to obtain the cylindrical preparation (the length of the preparation is 10 mm, the diameter of the preparation is 1.5 mm).

TABLE 6

| Vaccine M9 | |
|---|---|
| Ovalbumin | 0.6% |
| Porcine gamma globulin | 38% |
| Sodium chloride | 10% |
| Silicone | 48.4% |
| Aluminium hydroxide | 3% |
| Vaccine M11 | |
| Ovalbumin | 0.6% |
| Porcine gamma globulin | 38% |
| Sodium chloride | 10% |
| Silicone | 48.4% |
| Saponin | 3% |

EXPERIMENTAL PROCEDURE

Figure 1:
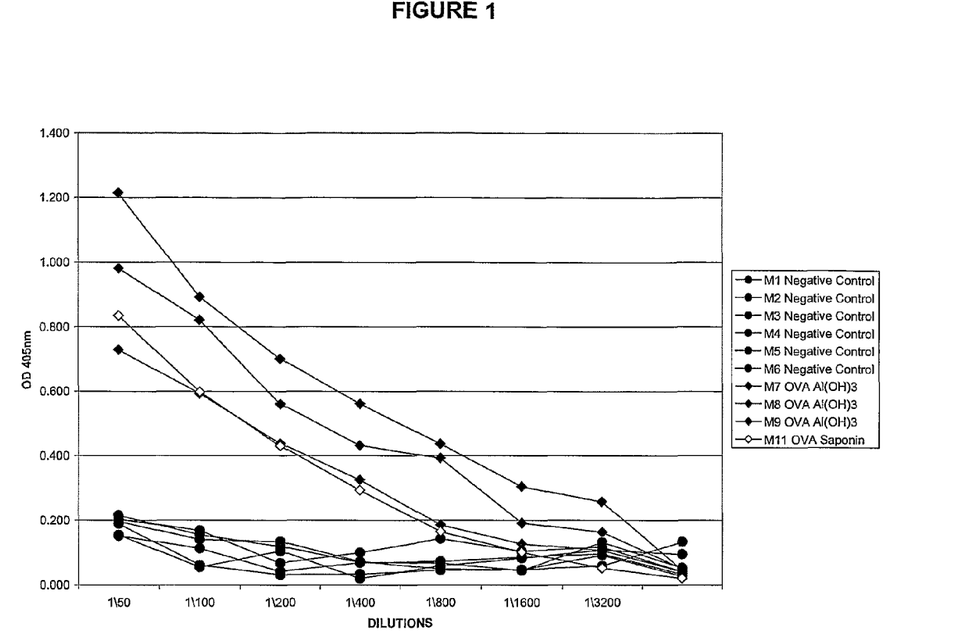

Mice injected intraperitoneally with implant measuring 1.5 mm (diameter)×10 mm length.
The implants fell into one of three categories:
(a) blank implant—negative control
(b) 100 µg OVA/Al(OH)$_3$
(c) 100 µg OVA/Saponin
Mice bled at day 10 after vaccination.
Titres measured for ovalbumin antibodies by ELISA.
Animals: Balb/c mice
Identification: Ear punch
Implants: Single formulation
The results are provided in FIG. 1.
Conclusion
Very high antibody titres were observed 10 days after vaccination for both preparations clearly showing that saponin and Al(OH)$_3$ are excellent adjuvants in the formulations.

EXAMPLE 4

*Salmonella* Vaccine in Horses

Purpose of the Study:
To evaluate the antibody response of horses to an experimental *Samonella* Newport inactivated vaccine comprising a bacterial extract of purified siderophore receptor and porin protein.
Animals:
4 yearling horses (≤1 year of age) maintained in a barn and on pasture
Vaccine:
Silicone covered rod 1.5 mm outside diameter, 1.3 mm internal diameter. Each horse received 2 implants of 2 cm on day 0 of the experiment either subcutaneously in the neck (2 horses) or intramuscular in the ligamentum nuchae area (2 horses).
Each 1 cm of implant contained 250 ug of *Salmonella* antigen adjuvanted with 3% aluminium hydroxide in powdered form (Sigma). The implants also contained 36% porcine γ globulin as a protection agent.
Vaccine Formulation:

| | % Formulation |
|---|---|
| Inactivated *Salmonella* Antigens | 1% |
| Adjuvant: Powdered Al(OH)$_3$ | 3% |
| NaCl | 10% |
| Protection Agent: Porcine γ-globulin | 36% |
| Silicone | 50% |

Figure 2:
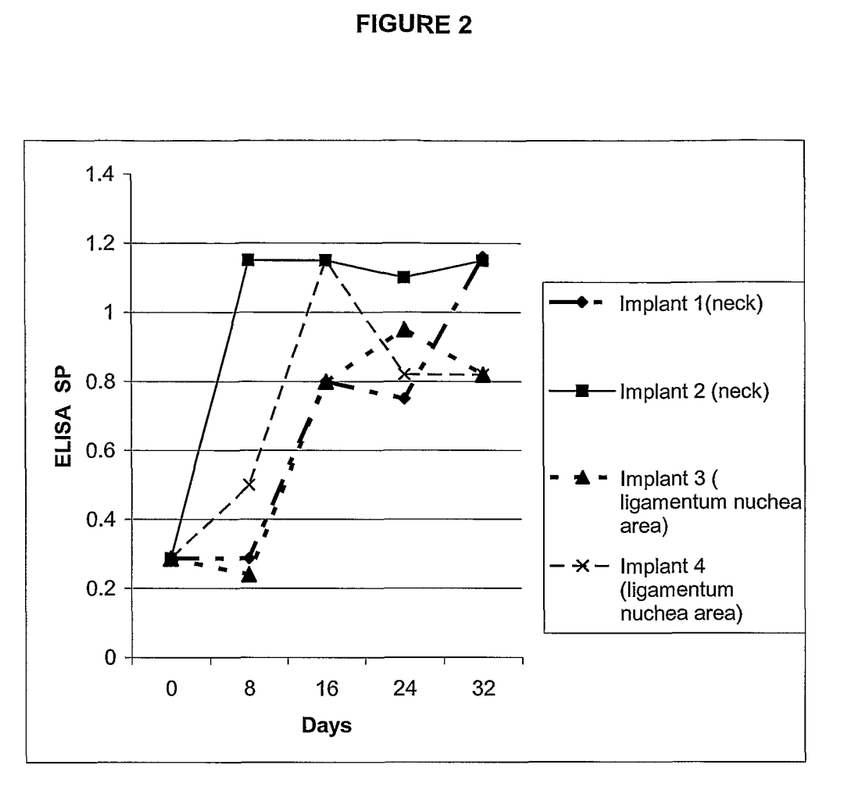

Samples:
Blood samples were taken from the jugular vein on days 0, 8, 16, 24 and 32 of the experiment and analysed by ELISA.
Site Reaction:
No site reactions were observed at anytime over the 32 days the results were recorded.
Results/Conclusions:
The results are summarized in FIG. 2. ELISA SP refers to signal-to-positive. The value given is the test value divided by a positive control. The results from ELISA assays from positive horse samples (from unreported work) were used as positive controls. A result of near 1 or greater is thus indicative of an excellent immune response.
All four horses showed a rapid onset of immunity to the antigen challenge with peak levels of antibody reached within 8 to 16 days. The results also show conclusively that Al(OH)$_3$ in a powdered form is an outstanding adjuvant. Both subcutaneous and intramuscular sites of implantation were successful with NO site reactions observed. This is an important finding as horses are extremely difficult to vaccinate being prone to adverse site reactions.

EXAMPLE 5

IBR Vaccine in Cattle

Purpose of the Study:

To evaluate the antibody response in healthy cattle against an inactivated infectious bovine rhinotracheitis (IBR) vaccine formulation as an aid in prevention of disease caused by Bovine Herpes Virus Types I & II.

Animals:

18 Angus steers, aged 12-15 months maintained on pasture.

Vaccine:

Silicone covered rod 1.5 mm outside diameter, 1.3 mm internal diameter. One group of 5 cattle received 1 implant of 2 cm in length, another group of 6 cattle received 2 implants of 2 cm in length and a third group of 7 cattle served as negative controls and were not vaccinated. The implants were administered subcutaneously in the ear.

Samples:

Blood samples were collected at 0, 5, 7, 14, 21, 28, 56 and 84 days after implantation.

Vaccine Formulation:

|  | % Formulation |
| --- | --- |
| Inactivated IBR Antigen* | 39.7% |
| Adjuvant: Saponin | 3.1% |
| NaCl | 10.2% |
| Silicone | 47% |

*includes high percentage of cell line debris and cell line culture media.

Site Reaction:

No site reactions were observed during the 84 days over which the study was conducted.

Results/Conclusions:

High antibody titres at day 28 after implantation (measured by ELISA) were observed in 4/5 cattle implanted with 1×2 cm implants, 4/6 cattle implanted with 2×2 cm implants and 0/7 cattle in the negative control group.

EXAMPLE 6

Neonatal Calf Diarrhea Vaccine in Cattle

Purpose of the Study:

To evaluate the antibody response of healthy, pregnant cows to aid in passive maternal immunisation of their calves (through the consumption of colostrum) against neonatal calf diarrhea caused by bovine rotavirus, bovine coronavirus and entertoxigenic strains of *Escherichia coli* having the K$_{99}$ pili adherence factor.

Animals:

142 pregnant dairy cows vaccinated 6-8 weeks prior to calving.

Vaccine:

Silicone covered rod 3.0 mm outside diameter, 2.8 mm internal diameter. Each cow received 2 implants of 2 cm subcutaneously in the ear.

Vaccine Formulation:

| Vaccine A | % Formulation |
| --- | --- |
| *Antigens: | 37% |
| Bovine Rotavirus, Bovine Coronavirus, | |
| K99 *E. coli* bacteria | |
| Adjuvant: Powdered Al(OH)3 | 3% |
| Protection Agent: Human γ-globulin | 11% |
| Silicone | 49% |

*includes high percentage of cell line debris, cell line culture media and bacterial culture media

| Vaccine S | % Formulation |
| --- | --- |
| *Antigens: | 37% |
| Bovine Rotuvirus, Bovine Coronavirus, | |
| K99 *Ecoli* bacteria | |
| Adjuvant: Saponin | 3% |
| Protection Agent: Human γ-globulin | 11% |
| Silicone | 50% |

*includes high percentage of cell line debris, cell line culture media and bacterial culture media Site Reaction:

All 142 cows implanted had their implant sites inspected 7 days after implantation in the ear.

| All values expressed as percentages | | |
| --- | --- | --- |
|  | Vaccine A | Vaccine B |
| No swelling in ear | 71 | 41 |
| Swelling <2 mm | 22 | 23 |
| Swelling <4 mm | 5 | 31 |
| Implant lost from ear | 2 | 4 |

Vaccine A which included the adjuvant powdered Al(OH)$_3$ proved to be an extremely non-reactive vaccine formulation. Vaccine B which included Saponin as the adjuvant was slightly more reactive as a vaccine formulation.

Results/Conclusions:

Both vaccine preparations showed a rapid onset of immunity (in sera obtained 7 days after implantation) to the 3 antigens in the formulations with very high titres being observed in the colostrum of all the 138 cows that retained the implants in the ear at calving.

EXAMPLE 7

Extended Milk Life Vaccine in Cattle

Purpose of the Study:

To evaluate over the lactation cycle of dairy cows for up to 305 days the antibody response of healthy lactating cows to a vaccine formulation containing bacterial antigens to prevent bacterial decay of milk held at room temperature.

Animals:

20 lactating cows vaccinated 4 weeks prior to calving.

Vaccine:

Silicone covered rod 1.5 mm outside diameter, 1.3 mm internal diameter. Each cow received 2 implants of 2 cm subcutaneously in the ear.

Vaccine Formulation:

| Vaccine A | % Formulation |
| --- | --- |
| Purified Bacterial Antigens | 1.1% |
| Adjuvant: Powdered Al(OH)3 | 3% |
| Protection Agent: Human γ-globulin | 35.7% |
| NaCl | 10.2% |
| Silicone | 50% |

| Vaccine S | % Formulation |
| --- | --- |
| Purified Bacterial Antigens | 1.1% |
| Adjuvant: Saponin | 3% |
| Protection Agent: Human γ-globulin | 35.7% |
| NaCl | 10.2% |
| Silicone | 50% |

Site Reaction:

No site reactions were observed in the ear of the 20 vaccinated cows.

Results/Conclusions:

The milk of all 20 cows, observed up to 100 days after lactation, contained antibodies that showed significant inhibition of bacterial growth in milk at room temperature for 2 days and under refrigeration for up to 10 days.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

The invention claimed is:

1. A sustained release vaccine apparatus selected from the group consisting of an implant, a pellet, a tablet and a solid gel, the apparatus including:
   a non-liquid vaccine composition including:
      one or more antigen component(s); and
      a pharmaceutically acceptable adjuvant therefor;
      optionally, a non-liquid vaccine protection agent,
      wherein the vaccine apparatus comprises a pharmaceutically acceptable non-liquid matrix comprising at least a water-soluble substance which is a polysaccharide, and a sustained release support material which is biocompatible and biodegradable material; and
   wherein the vaccine apparatus is for oral administration to a non-human animal without liquid formulation,
   and the vaccine apparatus upon administration at least initiates and/or stimulates an immune response in the non-human animal.

2. The sustained release vaccine apparatus according to claim 1, wherein the apparatus provides, in use, approximately zero order release of antigen.

3. The sustained release vaccine apparatus according to claim 1, further including a water soluble or insoluble pharmaceutically active component, or mixtures thereof.

4. The sustained release apparatus according to claim 1, wherein the one or more antigen component(s) are contained in first dry milled powder particles dispersed in the matrix, and wherein the pharmaceutically acceptable adjuvant is a non-liquid mineral salt adjuvant consisting of second dry milled powder particles dispersed in the matrix.

5. The sustained release vaccine apparatus of claim 4, wherein the non-liquid mineral salt adjuvant is dispersed in the matrix in the form of dry powder particles consisting of $Al(OH)_3$.

6. The sustained release vaccine apparatus of claim 4, which is in the form of a biocompatible and biodegradable pellet or tablet adapted for oral administration.

7. The sustained release vaccine apparatus of claim 1, wherein the matrix further comprises an oligosaccharide.

8. The sustained release vaccine apparatus of claim 7, wherein the oligosaccharide is trehalose.

9. The sustained release vaccine apparatus of claim 1, wherein the matrix further comprises an amphipathic substance.

10. The sustained release vaccine apparatus of claim 9, wherein the amphipathic substance is in the form of a dry powder consisting of saponin.

11. The sustained release vaccine apparatus of claim 9, wherein the amphipathic substance is dispersed in the matrix in the form of dry milled particles consisting of the amphipathic substance dispersed in the matrix.

12. The sustained release vaccine apparatus of claim 11, wherein the amphipathic substance is in the form of a dry powder consisting of saponin.

* * * * *